United States Patent
Ding et al.

(10) Patent No.: US 10,138,561 B2
(45) Date of Patent: Nov. 27, 2018

(54) CERIUM CITRATE, METHOD OF MAKING AND CORROSION INHIBITOR COMPRISING CERIUM CITRATE

(71) Applicant: United Technologies Corporation, Farmington, CT (US)

(72) Inventors: Zhongfen Ding, South Windsor, CT (US); Georgios S. Zafiris, Glastonbury, CT (US); Bart Antonie van Hassel, Weatogue, CT (US); Catalin G. Fotache, West Hartford, CT (US)

(73) Assignee: UNITED TECHNOLOGIES CORPORATION, Farmington, CT (US)

( * ) Notice: Subject to any disclaimer, the term of this patent is extended or adjusted under 35 U.S.C. 154(b) by 152 days.

(21) Appl. No.: 15/173,847

(22) Filed: Jun. 6, 2016

(65) Prior Publication Data
US 2017/0350019 A1    Dec. 7, 2017

(51) Int. Cl.
| | |
|---|---|
| *C07C 59/265* | (2006.01) |
| *C23F 13/00* | (2006.01) |
| *C23F 11/00* | (2006.01) |
| *C23F 13/06* | (2006.01) |
| *C23F 13/14* | (2006.01) |
| *C09D 5/00* | (2006.01) |
| *C07C 51/41* | (2006.01) |
| *C01F 17/00* | (2006.01) |
| *C09D 5/08* | (2006.01) |
| *C23F 11/10* | (2006.01) |

(Continued)

(52) U.S. Cl.
CPC ............ *C23F 13/005* (2013.01); *C01F 17/00* (2013.01); *C07C 51/412* (2013.01); *C07C 59/265* (2013.01); *C09D 5/00* (2013.01); *C09D 5/084* (2013.01); *C09D 7/61* (2018.01); *C23F 11/10* (2013.01); *C23F 11/18* (2013.01); *C23F 11/187* (2013.01); *C23F 13/06* (2013.01); *C23F 13/14* (2013.01)

(58) Field of Classification Search
CPC ...... C01F 17/00; C01F 17/0006; C07F 19/00; C07F 19/005; C07C 59/265; C07C 51/412; C08K 3/24
See application file for complete search history.

(56) References Cited

U.S. PATENT DOCUMENTS

| | | |
|---|---|---|
| 6,758,857 B2 | 7/2004 | Cioanta et al. |
| 7,341,677 B2 | 3/2008 | Yu et al. |

(Continued)

FOREIGN PATENT DOCUMENTS

| | | | |
|---|---|---|---|
| CN | 1484970 A | * | 3/2004 |
| CN | 101481510 A | | 7/2009 |

(Continued)

OTHER PUBLICATIONS

Partial machine translation of CN 1484970 A (2018).*

(Continued)

Primary Examiner — Kregg T Brooks
(74) Attorney, Agent, or Firm — Cantor Colburn LLP

(57) ABSTRACT

A method of making cerium citrate includes combining cerium carbonate and citric acid to produce cerium citrate and carbon dioxide. The cerium citrate is substantially free of negative ions other than citrate. The cerium citrate can be used in a corrosion inhibitor composition.

7 Claims, 1 Drawing Sheet

(51) Int. Cl.
 *C23F 11/18* (2006.01)
 *C09D 7/61* (2018.01)

(56) References Cited

U.S. PATENT DOCUMENTS

| | | |
|---|---|---|
| 7,972,533 B2 | 7/2011 | Jaworowski et al. |
| 2009/0117369 A1 | 5/2009 | Jaworowski et al. |
| 2014/0212354 A1 | 7/2014 | Arsenault-Preece et al. |

FOREIGN PATENT DOCUMENTS

| | | |
|---|---|---|
| EP | 1493846 A1 | 1/2005 |
| EP | 1842881 A1 | 10/2007 |
| EP | 2011899 A2 | 1/2009 |

OTHER PUBLICATIONS

European Search Report for European Application No. 17174490.7, dated Nov. 22, 2017, 5 pages.
James et al.; "Solvent-assisted mechanochemistry"; ChemComm; vol. 49, 2013; 16 pages.
Kaliaguine et al; "Perovskite-type oxides synthesized by reactive grinding: Part I. Preparation and characterization"; Applied Catalysis A: General; vol. 209; 2001; pp. 345-358.

\* cited by examiner

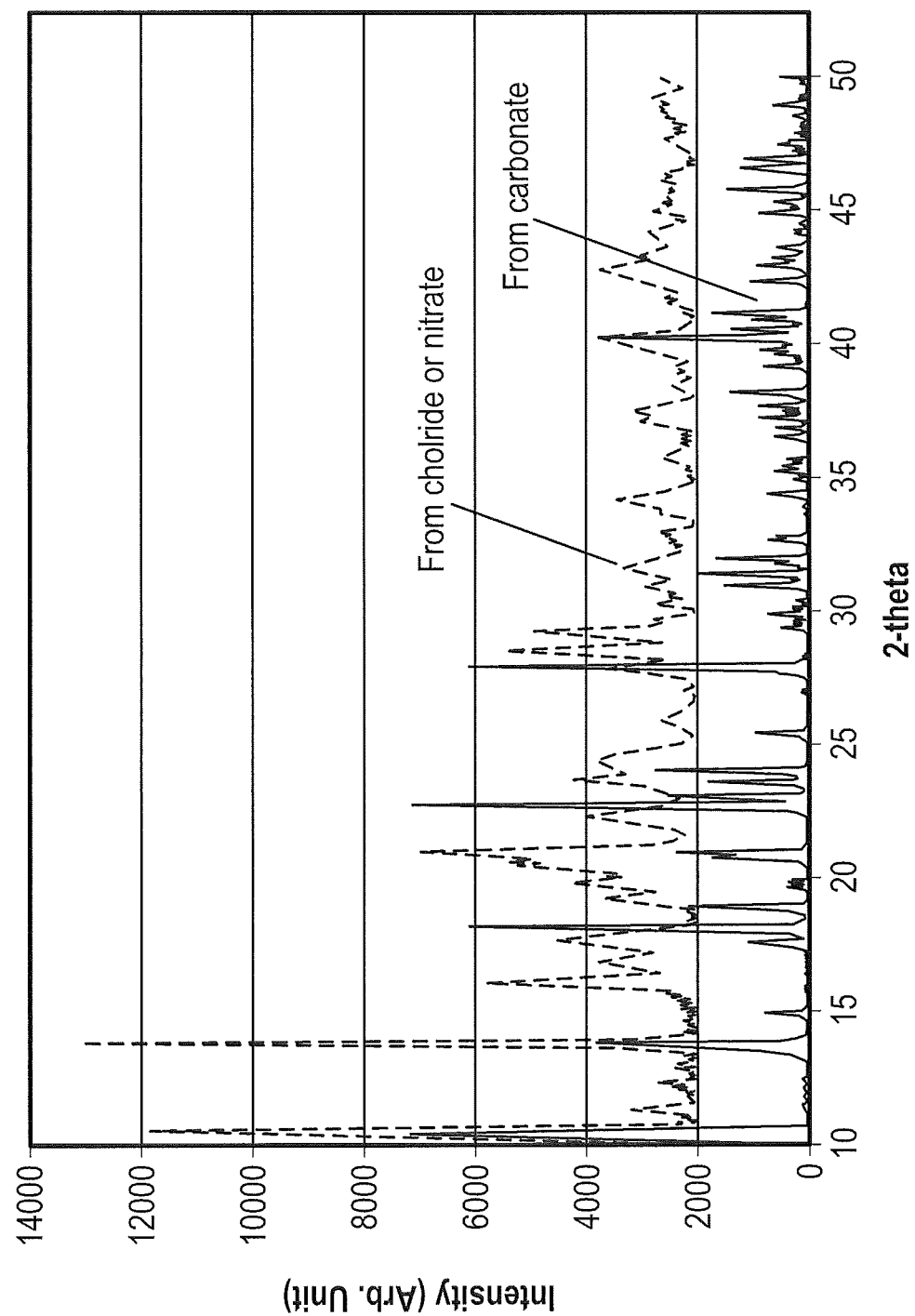

CERIUM CITRATE, METHOD OF MAKING AND CORROSION INHIBITOR COMPRISING CERIUM CITRATE

BACKGROUND

This disclosure relates to corrosion inhibitors and, more particularly, to methods of making corrosion inhibitors.

Components made from metallic alloys, such as aluminum alloys, achieve higher strengths through inclusion of alloying elements. However, the presence of these alloying elements tends to make the alloy vulnerable to corrosion. Typically, the component utilizes a protective coating containing a corrosion-inhibitor to protect the underlying alloy from corrosion.

One type of corrosion-inhibitor includes hexavalent chromium in the form of a barium or strontium chromate compound, for example. Although effective, hexavalent chromium is commonly recognized as a carcinogen and is therefore undesirable for use as a coating.

Chrome-free corrosion-inhibitors have been used as an alternative to hexavalent chromium inhibitors. For example, chrome-free corrosion inhibitors utilize anodic and cathodic corrosion inhibitors to resist corrosion of the underlying alloy.

The effectiveness of the anodic and cathodic corrosion inhibitors is related to their composition and availability for corrosion inhibition. Accordingly, it is desirable to provide improved methods for the synthesis of corrosion inhibitors to improve the quality and availability of the corrosion inhibitor.

SUMMARY

In some aspects of the disclosure, a method of making cerium citrate includes combining cerium carbonate and citric acid to produce cerium citrate and carbon dioxide.

In the method described above the cerium carbonate may be a hydrated cerium carbonate.

In any of the foregoing embodiments, the cerium carbonate and citric acid may be combined in the presence of a solvent.

In any of the foregoing embodiments, the method may further comprises washing the cerium citrate, drying the washed cerium citrate and reducing the dried cerium citrate to a fine powder.

In any of the foregoing embodiments, the cerium citrate may have greater than or equal to 5 weight percent water of hydration.

In any of the foregoing embodiments, the cerium citrate may be a trivalent cerium citrate.

In any of the foregoing embodiments, the cerium carbonate and citric acid may be subjected to high energy ball milling. The high energy ball milling may be performed using stainless steel, ceramic, or tungsten balls. The cerium carbonate may be a hydrate.

In another embodiment, a cerium citrate produced by combining cerium carbonate and citric acid is described and the cerium citrate is substantially free of negative ions other than citrate. The cerium citrate may be hydrated. When hydrated, the cerium citrate may have greater than or equal to 10 weight percent water of hydration. In any of the foregoing embodiments the cerium citrate may be a trivalent cerium citrate.

In another embodiment, a corrosion inhibitor composition includes a cerium citrate substantially free of negative ions other than citrate. The cerium citrate may be a hydrate. When the cerium citrate is a hydrate it may have greater than or equal to 10 weight percent water of hydration. In any of the foregoing embodiments the cerium citrate may be a trivalent cerium citrate. In any of the foregoing embodiments the corrosion inhibitor composition may include zinc molybdate. The corrosion inhibitor composition of any of the foregoing embodiments may be combined with at least one of an adhesive, primer, paint, lubricant, cooling fluid, sealant and epoxy.

Also described herein is a metal substrate and a corrosion inhibitor disposed on the substrate, wherein the corrosion inhibitor includes a cerium citrate substantially free of negative ions other than citrate.

The foregoing features and elements may be combined in various combinations without exclusivity, unless expressly indicated otherwise. These features and elements as well as the operation thereof will become more apparent in light of the following description and the accompanying drawings. It should be understood, however, that the following description and drawings are intended to be illustrative and explanatory in nature and non-limiting.

BRIEF DESCRIPTION OF THE DRAWINGS

The subject matter which is regarded as the present disclosure is particularly pointed out and distinctly claimed in the claims at the conclusion of the specification. The foregoing and other features, and advantages of the present disclosure are apparent from the following detailed description taken in conjunction with the accompanying drawing in which:

FIG. 1 shows the x-ray diffraction patterns for cerium citrate synthesized from cerium carbonate, cerium nitrate and cerium chloride.

DETAILED DESCRIPTION

Cerium citrate is a cathodic corrosion inhibitor for aluminum alloys. Surprisingly, it has been found that the method of synthesis of the cerium citrate can affect its effectiveness as a corrosion inhibitor. Typically, cerium citrate has been made using cerium chloride or cerium nitrate as a starting material. Unfortunately, the negative ion components of these compounds, the chloride and the nitrate, when released during the synthesis of cerium citrate can adsorb to the cerium citrate surface. These negative ions are then included in the corrosion inhibitor composition and can harm the corrosion protection due to ionic mobility and result in corrosion issues. As a result of this discovery a new method of cerium citrate synthesis was required, one in which the issues of negative ion adsorption would be avoided.

Disclosed herein is a method of making cerium citrate comprising reacting cerium carbonate hydrate with citric acid as shown in formula (1)

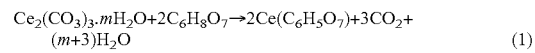

$$Ce_2(CO_3)_3 \cdot mH_2O + 2C_6H_8O_7 \rightarrow 2Ce(C_6H_5O_7) + 3CO_2 + (m+3)H_2O \tag{1}$$

Advantageously a product of the reaction is carbon dioxide which is not ionic and is typically a gas under the reaction conditions. Hence, the carbon dioxide product is not adsorbed to the surface of the cerium citrate and the cerium citrate produced in this manner does not comprise negative ions that affect the corrosion protection in a negative manner. Additionally, it should be noted that the cerium citrate produced using cerium carbonate as a starting material has a different crystal structure than cerium citrate produced using either cerium nitrate or cerium chloride as a starting material. The cerium carbonate hydrate shown in formula (1) has a hydration level m and m can have a value of 0 to 10, or, 1 to 9, or, 2 to 8. The cerium citrate produced by the reaction can be a trivalent cerium citrate.

The reaction described by formula (1) can be performed by combining cerium carbonate hydrate, citric acid and a solvent in an inert atmosphere. The cerium carbonate hydrate and citric acid are combined in a molar ratio of 1:1 to 1:3, or 1:2 to 1:2.5, or 1:2.1. Useful solvents include water and polar protic solvents having a low boiling point such as methanol, ethanol, and propanol. The inert atmosphere typically comprises nitrogen or argon or other inert gas. The inert gas is employed to prevent or limit oxidation of the cerium ion during cerium citrate synthesis. Carbon dioxide is not a useful gas for the inert atmosphere as it would impede or slow the progress of the reaction. The reaction may be performed at a temperature of 50 to 90° C. for 5 to 7 hours. Within this range the temperature can be 60 to 80° C. The reaction time can be 5.5 to 6.5 hours. At this point the reaction may have a pH of 1 to 3. The reaction is then cooled to room temperature. After the reaction is cooled to room temperature additional cerium carbonate hydrate can be added. The reaction is continued for another 8 to 12 hours. At this point the reaction may have a pH of 6 to 7.

The reaction product, cerium citrate, can be isolated by a solid separation method such as filtration, centrifugation, or vacuum evaporation. Following separation the product is typically washed with deionized water to remove any remaining citric acid. After washing the cerium citrate can be dried. Drying can occur at a temperature of 50° C. to 85° C. for 4 to 12 hours. In some embodiments a vacuum oven is used. Drying is not intended to remove all waters of hydration from the cerium citrate. In some embodiments the cerium citrate has greater than or equal to 5 weight percent water of hydration, or greater than or equal to 10 weight percent water of hydration. When the water of hydration is less than 10 weight percent, the corrosion inhibiting performance of the cerium citrate may be decreased. After drying, the resulting material can be reduced in size to a fine powder by milling, grinding or a combination thereof.

The reaction described by formula (1) can also be performed using high energy ball milling. The cerium carbonate and citric acid can be combined in amounts as described above. The cerium carbonate is preferably a hydrate although a hydrated cerium carbonate is not required. The reactants are combined in a container, typically stainless steel or tungsten lined, with stainless steel, ceramic or tungsten balls of the desired number and size. The number and size of the balls is typically dictated by the size of the container and the amount of material being reacted. For example, 2.88 grams of cerium carbonate hydrate and 1.92 grams of citric acid can be combined with about a dozen of ceramic balls having a diameter of 0.25 inches in a cylindrical stainless steel autoclave (1.5 inch inner diameter, 2.25 inch in height) having a volume of 65 milliliters with a pressure relief valve. The container is purged with an inert gas such as nitrogen or argon, then placed in a shaker mill or similar device and agitated at a speed of 30 to 720 rotations per minute (rpm). If the cerium carbonate employed is not a hydrate then the reaction may be facilitated by the addition of a small amount of solvent or water, for example, 10 to 1000 microliters of water per gram of cerium carbonate. Agitation continues for approximately 60 hours. After the reaction is complete the product is washed to remove any excess citric acid, dried and reduced to a fine powder as described above.

The cerium citrate produced as described herein is substantially free of negative ions other than citrate. Substantially free, as used in this context, is defined as containing less than 1 weight percent (wt %) based on the total weight of the material, or, less than 0.1 wt % of a negative ion other than citrate.

The cerium citrate substantially free of negative ions other than citrate can be used in a corrosion inhibitor composition. The corrosion inhibitor composition can further comprise anodic corrosion inhibitors such as molybdates, permanganates, tungstates, and/or vanadates. In some embodiments the corrosion inhibitor composition further comprises zinc molybdate.

The corrosion inhibitor composition may be included in adhesives, paints and primers, organic sealants, epoxies, cooling fluids, lubricants, and the like (hereafter referred to as a carrier fluid). These products may be applied to a metal substrate that is being protected by any suitable manner such as spraying, brushing, dipping, or the like. In addition, the corrosion inhibitor composition may be dissolved in a carrier such as alcohol, water or the like and formed on the surface of a substrate as a conversion coating.

The corrosion inhibitor composition is particularly useful in preventing general corrosion and pitting corrosion on metal substrates, particularly, high strength aluminum alloys for use in the aerospace industry. The corrosion inhibitor composition may be applied in any manner known in the art including as a conversion coating, or applied as a primer, adhesive, epoxy, paint, organic sealant, sealer for anodized aluminum, additive for recirculating water system or the like.

EXAMPLES

Cerium citrate samples synthesized from cerium carbonate, cerium nitrate and cerium chloride using wet chemistry were compared using x-ray diffraction (XRD) as shown in FIG. 1. Cerium citrate synthesized from carbonate has one type of powder diffraction structure (type I), which is different from cerium citrate synthesized from nitrate or chloride (which have type II structure). The cerium citrate synthesized from three different starting materials was each combined with an anodic corrosion inhibitor. The corrosion inhibiting properties were evaluated by comparing the corrosion current (in milliamperes per square centimeter) in an aqueous solution comprising 350 ppm NaCl. Lower corrosion current indicates better corrosion inhibiting performance. Results are shown in Table 1.

TABLE 1

|  | XRD structure | Corrosion Current ($mA/cm^2$) in 350 ppm NaCl |
| --- | --- | --- |
| Cerium citrate from carbonate | Type I | 0.02-0.08 |
| Cerium citrate from chloride | Type II | 0.2-0.3 |
| Cerium citrate from nitrate | Type II | 0.03-0.04 |

The effect of hydrated water was also examined. Cerium citrate was synthesized from cerium carbonate and had differing levels of hydration. 1.92 grams of citric acid was dissolved in 50 milliliters of deionized water. The mixture was heated to 80° C. 2.88 grams of cerium carbonate hydrate was added slowly over an hour. The reaction was continued for 6 hours and the pH of the reaction mixture was 1-3 (by pH paper). The reaction mixture was cooled and an additional 0.288 grams of cerium carbonate was added slowly and allowed to react overnight. The pH of the reaction mixture was 6-7 at the end of the overnight period. The material was filtered, washed with deionized water and dried in an oven. One sample dried at 60° C. overnight had greater than 10 wt % water whereas one sample dried at 90° C. overnight had less than 10 wt % water. The cerium citrate with differing water content was each combined with the same anodic corrosion inhibitor. The corrosion inhibiting properties were evaluated by comparing the corrosion current (in milliamperes per square centimeter) in an aqueous solution comprising 350 ppm NaCl. Lower corrosion current indicates better corrosion inhibiting performance. Results are shown in Table 2.

TABLE 2

|  | Water content | Corrosion Current ($mA/cm^2$) in 350 ppm NaCl |
|---|---|---|
| Cerium citrate from carbonate | <10 wt % | 1.0-1.3 |
| Cerium citrate from carbonate | >10 wt % | 0.1-0.3 |

The use of the terms "a," "an," "the," and similar references in the context of description (especially in the context of the following claims) are to be construed to cover both the singular and the plural, unless otherwise indicated herein or specifically contradicted by context. All ranges disclosed herein are inclusive of the endpoints, and the endpoints are independently combinable with each other.

While the present disclosure has been described in detail in connection with only a limited number of embodiments, it should be readily understood that the present disclosure is not limited to such disclosed embodiments. Rather, the present disclosure can be modified to incorporate any number of variations, alterations, substitutions, combinations, sub-combinations, or equivalent arrangements not heretofore described, but which are commensurate with the scope of the present disclosure. Additionally, while various embodiments of the present disclosure have been described, it is to be understood that aspects of the present disclosure may include only some of the described embodiments.

Accordingly, the present disclosure is not to be seen as limited by the foregoing description, but is only limited by the scope of the appended claims.

What is claimed is:

1. A method of making cerium citrate comprising combining cerium carbonate and citric acid at a temperature of 60 to 90° C. for 5 to 7 hours in an inert atmosphere and cooling and reacting for 8 to 12 hours to produce cerium citrate and carbon dioxide.

2. The method of claim 1, wherein the cerium carbonate is a hydrated cerium carbonate.

3. The method of claim 1, wherein the cerium carbonate and citric acid are combined in the presence of a solvent.

4. The method of claim 1, further comprising washing the cerium citrate, drying the washed cerium citrate and reducing the size of the dried cerium citrate particles.

5. The method of claim 1, wherein the cerium citrate has greater than or equal to 5 weight percent water of hydration.

6. The method of claim 1, wherein the cerium citrate is a trivalent cerium citrate.

7. The method of claim 1, wherein the cerium citrate has greater than or equal to 10 weight percent water of hydration.

* * * * *